(12) United States Patent
Grasso et al.

(10) Patent No.: US 10,195,254 B2
(45) Date of Patent: Feb. 5, 2019

(54) MYRISTOYLATED LEPTIN-RELATED PEPTIDES AND USES THEREOF

(71) Applicant: ALBANY MEDICAL COLLEGE, Albany, NY (US)

(72) Inventors: Patricia Grasso, Schenectady, NY (US); Zachary Novakovic, Erie, PA (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 4 days.

(21) Appl. No.: 15/510,051

(22) PCT Filed: Aug. 11, 2015

(86) PCT No.: PCT/US2015/044618
§ 371 (c)(1),
(2) Date: Mar. 9, 2017

(87) PCT Pub. No.: WO2016/025459
PCT Pub. Date: Feb. 18, 2016

(65) Prior Publication Data
US 2017/0312340 A1 Nov. 2, 2017

Related U.S. Application Data

(60) Provisional application No. 62/035,916, filed on Aug. 11, 2014.

(51) Int. Cl.
| | | |
|---|---|---|
| *A61K 38/08* | (2006.01) | |
| *A61K 38/22* | (2006.01) | |
| *A61K 38/10* | (2006.01) | |
| *A61K 9/08* | (2006.01) | |
| *A61K 38/00* | (2006.01) | |

(52) U.S. Cl.
CPC .......... *A61K 38/2264* (2013.01); *A61K 38/08* (2013.01); *A61K 38/10* (2013.01); *A61K 9/08* (2013.01); *A61K 38/00* (2013.01)

(58) Field of Classification Search
CPC ..... A61K 38/2264; A61K 38/08; A61K 38/10
See application file for complete search history.

(56) References Cited

U.S. PATENT DOCUMENTS

| | | | | |
|---|---|---|---|---|
| 6,475,984 B2 * | 11/2002 | Kirwin | ............... | A61K 9/5015 514/4.8 |
| 6,777,388 B1 * | 8/2004 | Grasso | ............... | A61K 48/00 514/4.8 |
| 2011/0046058 A1 | 2/2011 | Maggio et al. | | |
| 2011/0288009 A1 | 11/2011 | Castaigne et al. | | |

FOREIGN PATENT DOCUMENTS

| | | |
|---|---|---|
| WO | 2012054500 A2 | 4/2012 |
| WO | 2012158962 A2 | 11/2012 |

OTHER PUBLICATIONS

Grasso et al., Endocrinol. 138: 1413-1418, 1997.*
Campfield et al., Science 280: 1383-1387, 1998.*
Rohner-Jearnrenaud et al., The New Eng. J. Med., 334: 324-325, 1996.*
Hayashi and Titani, Proc. Jpn Acad. Ser. B 86: 494-508, 2010.*
Martin et al., Biochemie 93: 18-31, 2011.*
International Search Report Form PCT/ISA/220, International Application No. PCT/US15/44618, pp. 1-10, dated Mar. 17, 2016.
Novakovic, Zachary M., Brian M. Anderson and Patricia Grasso. "Myristic acid conjugation of [D-Leu-4]-OB3, a biologically active leptin-related synthetic peptide amide, significantly improves its pharmacokinetic profile and efficacy." Peptides 62 (2014): 176-182.
Lee D. W. et al., "Oral delivery of mouse (D-Leu-4)-OB3, a synthetic peptide amide with leptin-like activity, in male Swiss Webster mice: A study comparing the pharmacokinetics of oral delivery to intraperitoneal, subcutaneous, intramuscular, and intranasal administration", Regulatory Peptides, Elsevier Science BV, NL, vol. 160, No. 1-3, Feb. 25, 2010, pp. 129-132, XP026874075, ISSN: 0167-0115.
Allison R. Nelson, et al., "Myristoyl-Based Transport of Peptides into Living Cells +", Biochemistry, vol. 46, No. 51, Dec. 1, 2007, pp. 14771-14781, XP055398482, US, ISSN: 0006-2960, DOI: 10.1021/bi701295k.
Gault V. A. et al.,: "Administration of an acylated GLP-1 and GIP preparation provides added beneficial glucose-lowering and insulinotropic actions over single incretins in mice with Type 2 diabetes and obesity" Clinical Science vol. 34, No. 3, Apr. 15, 2011, pp. 331-117, XP055131264, ISSN: 0143-5221, DOI: 10.1042/CS20110006.
European Search Report EP15832443, EPO Form 1503, pp. 1-2, Completion of Search Mar. 6, 2018. Annex to the European Search Report EP Form P0459, pp. 1-8.

\* cited by examiner

*Primary Examiner* — Gyan Chandra
(74) *Attorney, Agent, or Firm* — Bond Schoeneck and King PLLC; David Nocilly

(57) ABSTRACT

A pharmaceutical compound for the treatment of obesity related disorder that is a conjugate of myristic acid and a leptin-related peptide. Preferably, the leptin-related peptide is OB3 that has been D-substituted at Leu-4. The resulting conjugate significantly improved the pharmacokinetic profile of the leptin-related peptide by extending its half-life from less than one hour to as long as twenty-eight hours, depending on the route of delivery, increasing uptake, reducing the rate of plasma clearance, and enabling the minimal effective dose to be reduced several fold.

7 Claims, 10 Drawing Sheets

Specification includes a Sequence Listing.

```
SEQUENCE LISTING

<160> NUMBER OF SEQ ID NOS: 16

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 1

Ser Cys Ser Leu Pro Gln Thr
1               5

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 2

Ala Val Pro Ile Gln Lys Val Gln Asp Asp Thr Lys Thr Leu Ile
1               5                   10                  15
```

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 3

Thr Lys Thr Leu Ile Lys Thr Ile Val Thr Arg Ile Asn Asp Ile
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 4

Arg Ile Asn Asp Ile Ser His Thr Gln Ser Val Ser Ala Lys Gln
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 5

Val Ser Ala Lys Gln Arg Val Thr Gly Leu Asp Phe Ile Pro Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 6

Asp Phe Ile Pro Gly Leu His Pro Ile Leu Ser Leu Ser Lys Met
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 7

Ser Leu Ser Lys Met Asp Gln Thr Leu Ala Val Tyr Gln Gln Val
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

```
<400> SEQUENCE: 8

Val Tyr Gln Gln Val Leu Thr Ser Leu Pro Ser Gln Asn Val Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 9

Ser Gln Asn Val Leu Gln Ile Ala Asn Asp Leu Glu Asn Leu Arg
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 10

Asp Leu Leu His Leu Leu Ala Phe Ser Lys Ser Cys Ser Leu Pro
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 11

Ser Cys Ser Leu Pro Gln Thr Ser Gly Leu Gln Lys Pro Glu Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 12

Gln Lys Pro Glu Ser Leu Asp Gly Val Leu Glu Ala Ser Leu Tyr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 13

Glu Ala Ser Leu Tyr Ser Thr Glu Val Val Ala Leu Ser Arg Leu
1               5                   10                  15

<210> SEQ ID NO 14
<211> LENGTH: 15
```

```
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 14

Ala Leu Ser Arg Leu Gln Gly Ser Leu Gln Asp Ile Leu Gln Gln
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 15

Asp Ile Leu Gln Gln Leu Asp Val Ser Pro Glu Cys
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide corresponding to OB3 region
      of leptin

<400> SEQUENCE: 16

Ser Cys His Leu Pro Trp Ala
1               5
```

MYRISTOYLATED LEPTIN-RELATED PEPTIDES AND USES THEREOF

CROSS-REFERENCE TO RELATED APPLICATIONS

The present application claims priority to U.S. Provisional Application No. 62/035,916, filed on Aug. 11, 2014.

BACKGROUND OF THE INVENTION

1. Field of the Invention

The present invention relates to leptin-related peptides and, more particularly, to myristoylated leptin-related peptides.

2. Description of the Related Art

Obesity, defined as an excess of body fat relative to lean body mass, is associated with numerous, important clinical and psychological morbidities, such as hypertension, elevated blood lipids, and Type II or non-insulin-dependent diabetes mellitus (NIDDM), and decreased life expectancy. There are approximately 6-10 million individuals with NIDDM in the United States, including 18% of the total population over 65 years of age. In addition, approximately 45% of males and 70% of females with NIDDM are obese, and their diabetes is substantially improved or even eliminated by weight reduction.

Leptin-related peptides and analogs have demonstrated great potential in treating human obesity and its related dysfunctions. On-going efforts in the design, development, and preclinical application of lepin-related synthetic peptide agonists and antagonists indicates that the apparent failure of leptin in the clinic to satisfy the therapeutic needs of the majority of obese humans has acted as a catalyst in efforts to develop novel peptide therapeutics targeted at reducing the pandemic proportions of this disease and its associated metabolic dysfunctions. In this regard, small-molecule peptide therapeutics have the potential to overcome the limitations of recombinant leptin, since their uptake into the central nervous system (CNS) is not dependent on saturable transport across the blood-brain barrier (BBB). Defective transport into the CNS has been identified as the cause of leptin resistance in the majority of cases of human obesity For example, synthetic peptides with leptin-like activity, such as mouse [D-Leu-4]-OB3 and its analogs, significantly influence body weight gain, food and water intake, blood glucose, insulin sensitivity, and serum osteocalcin, a sensitive and specific marker of bone turnover, in leptin-deficient ob/ob and leptin-resistant db/db mouse models. However, the pharmacokinetics of [D-Leu-4]-OB3 and its analogs as drug candidates in humans are not as optimal as needed for therapeutic uses. In particular, [D-Leu-4]-OB3 and its analogs have short serum half-life and high rate of plasma clearance, resulting in reduced bioavailability of [D-Leu-4]-OB3 and its analogs and thus higher dose required.

Accordingly, there is a need for the development of modified leptin-related peptides and analogs with improved pharmacokinetics to provide an effective therapeutic for the treatment of human obesity and its related dysfunctions.

BRIEF SUMMARY OF THE INVENTION

The present invention comprises a polypeptide conjugate of myristic acid and a leptin-related peptide that provides improved pharmacologic effects over non-myristic acid conjugated leptin-related peptides. Preferably, the myristic acid is conjugated to the N-terminus of the leptin-related peptide. The polypeptide conjugate herein can modulate body mass by reducing body weight gain, food intake, water consumption, and/or blood glucose levels following administration. The polypeptide conjugate herein also can increase bone formation.

In one embodiment of the invention, the leptin-related peptide comprises [D-Leu-4]-OB3, a synthetic peptide amide with leptin-like activity that has the sequence SCSLPQT (SEQ ID NO:1), and is conjugated to myristic acid to form the compound MA-[D-Leu-4]-OB3.

The pharmaceutical composition described herein may be administered at a dosage that is at least 4-fold, and even 10-fold, lower than the dosage of a non-myristoylated leptin-related peptide. The myristic acid conjugated leptin-related peptide may be used to treat a condition relating to homeostasis of body mass in a subject in need thereof by administering to the subject a therapeutically effective amount. For example, the treated condition may be obesity, hyperglycemia, hyperinsulinemia, hyperphagia, thyroid dysfunction, infertility or diabetes. The myristic acid conjugated leptin-related peptide may also be used to increase bone formation. For example, the myristic acid conjugated leptin-related peptide may be used to treat a subject suffering from a disorder selected from the group consisting of malnutrition, starvation, anorexia nervosa, osteoporosis, cancer, diabetes, tuberculosis, chronic diarrhea, AIDS, and Superior mesenteric artery syndrome. The myristic acid conjugated leptin-related peptide may be administered via subcutaneous, intraperitoneal, intramuscular, oral or intranasal administration.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of a myristic acid conjugated leptin-related peptide according to the present invention.

FIG. 2 is a graph showing serum concentrations of MA-[D-Leu-4]OB3 before treatment (time 0) and 1, 2, 4, 6, 18, and 24 hours after subcutaneous delivery of 0.1 mg of peptide to male Swiss Webster mice (n=3 mice per time point). Each value represents mean±SEM. Error bars are contained within the point and ranged between 0.01 and 0.12 ng/ml;

FIG. 3 is a graph showing serum concentrations of MA-[D-Leu-4]OB3 before treatment (time 0) and 1, 2, 4, 6, 18, and 24 hours after intraperitoneal delivery of 0.1 mg of peptide to male Swiss Webster mice (n=3 mice per time point). Each value represents mean±SEM. Error bars are contained within the point and ranged between 0.01 and 0.12 ng/ml;

FIG. 4 is a graph showing serum concentrations of MA-[D-Leu-4]OB3 before treatment (time 0) and 1, 2, 4, 6, 18, and 24 hours after intramuscularl delivery of 0.1 mg of peptide to male Swiss Webster mice (n=3 mice per time point). Each value represents mean±SEM. Error bars are contained within the point and ranged between 0.01 and 0.12 ng/ml;

FIG. 5 is a graph showing serum concentrations of MA-[D-Leu-4]OB3 before treatment (time 0) and 1, 2, 4, 6, 18, and 24 hours after oral delivery (gavage) of 0.1 mg of peptide to male Swiss Webster mice (n=3 mice per time point). Each value represents mean±SEM. Error bars are contained within the point and ranged between 0.01 and 0.12 ng/ml;

FIG. 6 is a graph showing serum concentrations of MA-[D-Leu-4]OB3 before treatment (time 0) and 1, 2, 4, 6, 18, and 24 hours after intranasal instillation of 0.1 mg of peptide to male Swiss Webster mice (n=3 mice per time point). Each value represents mean±SEM. Error bars are contained within the point and ranged between 0.01 and 0.12 ng/ml;

Figure 9:
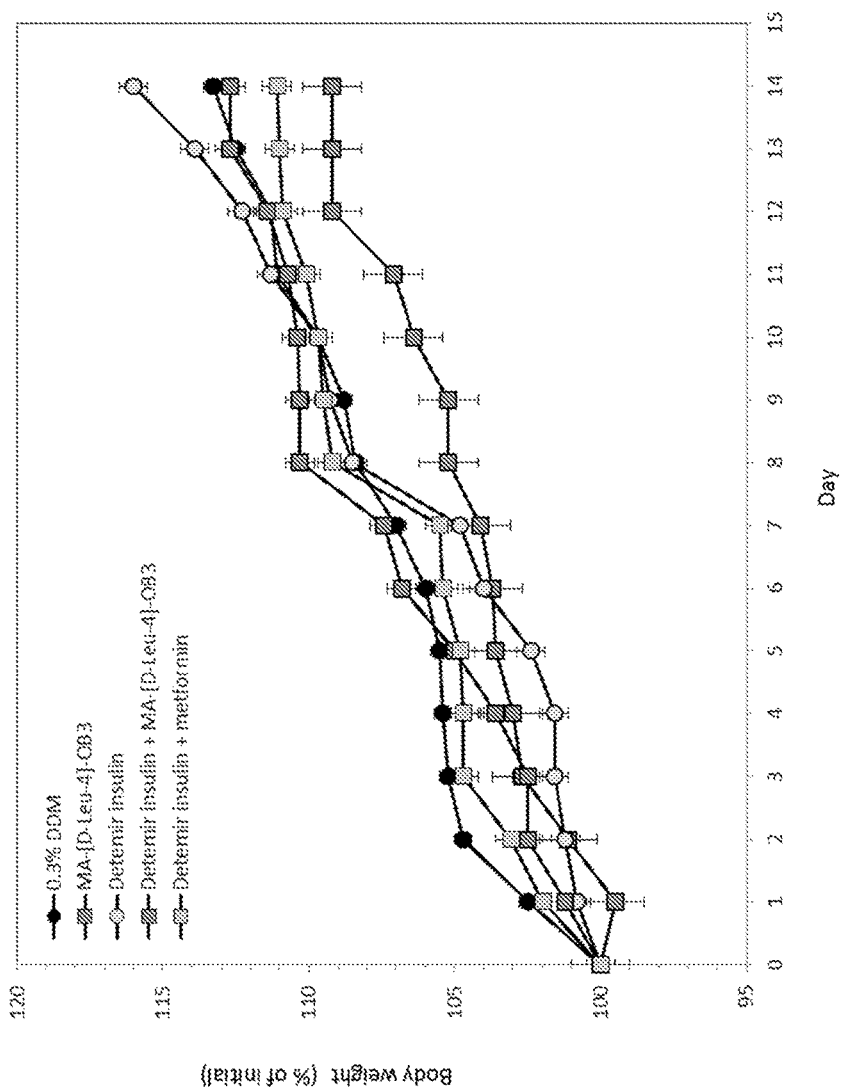
Figure 10:
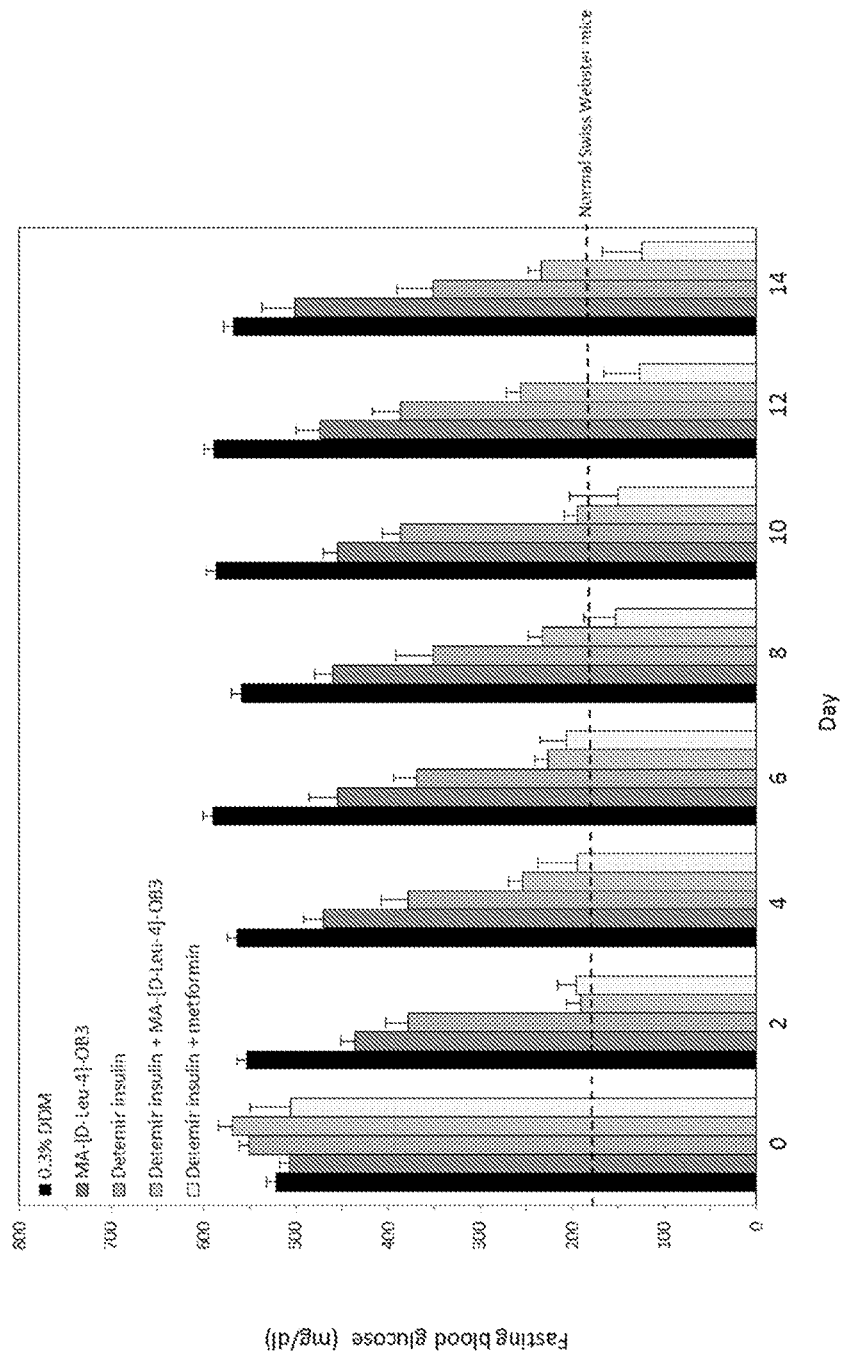

FIG. 9 is a graph showing the effects of detemir insulin, in the absence or presence of MA-[D-Leu-4]-OB3 or metformin, on body weight gain in STZ-induced hyperglycemic male Swiss Webster mice. Each point represents mean±SEM body weight, expressed as percent of initial (n=6 mice per group); and FIG. 10 is a graph showing the effects of detemir insulin, in the absence or presence of MA-[D-Leu-4]-OB3 or metformin, on fasting blood glucose levels in STZ-induced hyperglycemic male Swiss Webster mice. Each bar and vertical line represents mean±SEM fasting blood glucose (n=6 mice per group).

DETAILED DESCRIPTION OF THE INVENTION

Figure 1:
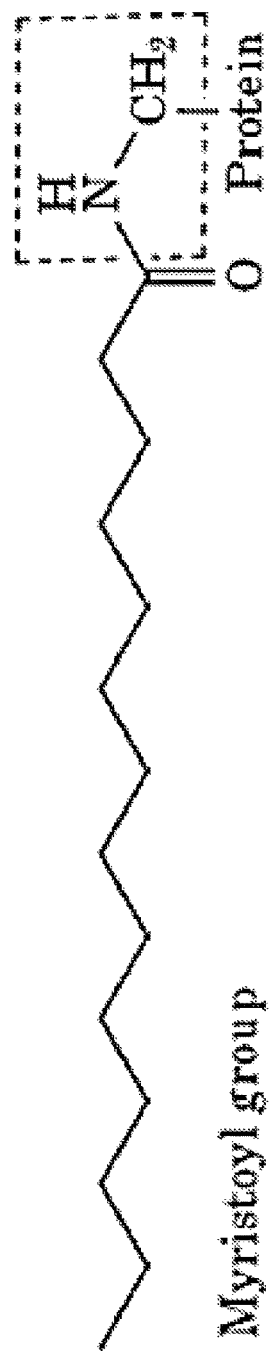

Referring now to the drawings, wherein like reference numerals refer to like parts throughout, there is seen in FIG. 1 a conjugate of myristic acid and a leptid-related peptide that results in a significantly improved pharmacokinetic profile over the leptin-related protein alone. Preferably, the leptin-related peptide is the synthetic peptide known as OB3 that corresponds to residues 116-122 of leptin, where mouse OB3 has the sequence SCSLPQT (SEQ ID NO:1) and human OB3 has the sequence SCHLPWA (SEQ ID NO: 16).

The leptin-related peptide may also comprise other region leptin that are proximate to or overlap the regions that correspond to SCSLPQT (SEQ ID NO:1) and SCHLPWA (SEQ ID NO: 16). For example, AVPIQKVQDDTKTLI (SEQ ID NO: 2); TKTLIKTIVTRINDI (SEQ ID NO: 3); RINDISHTQSVSAKQ (SEQ ID NO: 4); VSAKQRVT-GLDFIPG (SEQ ID NO: 5); DFIPGLHPILSLSKM (SEQ ID NO: 6); SLSKMDQTLAVYQQV (SEQ ID NO: 7); VYQQVLTSLPSQNVL (SEQ ID NO: 8); SQNVLQ-IANDLENLR (SEQ ID NO: 9); DLLHLLAFSKSCSLP (SEQ ID NO: 10); SCSLPQTSGLQKPES (SEQ ID NO: 11); QKPESLDGVLEASLY (SEQ ID NO: 12); EASLYSTEVVALSRL (SEQ ID NO: 13); ALSRLQG-SLQDILQQ (SEQ ID NO: 14); or DILQQLDVSPEC (SEQ ID NO: 15) could be evaluated using the protocol below.

Preferably, the leptin-related peptide includes at least one D-substituted amino acid. For example, the D-isoform amino acid may be selected from the group consisting of [D-Ser-1]; [D-Cys-2]; [D-Ser-3]; [D-Leu-4]; [D-Pro-5]; [D-Gln-6]; and [D-Thr-7] with respect to SEQ ID NO. 1 and may be selected from the group consisting of [D-Ser-1]; [D-Cys-2]; [D-His-3]; [D-Leu-4]; [D-Pro-5]; [D-Trp-6]; and [D-Ala-7] with respect to SEQ. ID. NO. 16.

As seen in FIG. 1, myristic acid is covalently attached to a free amino group of a residue of the leptin-related peptide. Alternatively, the myristic acid may be conjugated to any free amino group of a residue of the peptide. For example, the histidine (H) residue at position 3 of human OB3 peptide (SEQ ID NO: 16) provides an additional free amino group besides the alpha-amino group. The following lipids may also be used in lieu of myristic acid and testing according to the protocol below: cyclohexylvaleroyl, acyl-glutamyl, lauroyl, 2-succinylamido myristic acid, 2-succinylamidoethyl-oxy palmitic acid, myristoyl-α-glutamyl, myristoyl-α-glutamyl-glycyl, choloyl, 7-deoxycholoyl, lithocholoyl, lithocholoyl-glutamyl, 4-benzoyl-phenylalanine, L-thyroxyl, suberoyl-D-thyroxine, 3,3',5,5'-tetraiodothyroacetyl, cyclohexylvaleroyl.

The synthesis of the claimed invention is based on the known process of acylation, where fatty acids are covalently attached to proteins. To selectively acylate (e.g., myristoylate) the ε-amino group, various protecting groups may be used to block the α-amino group during the coupling. The selection of a suitable protecting group is known to one skilled in the art and includes p-methoxybenzoxy-carbonyl (pmZ). Preferably, the ε-amino group is acylated (e.g., myristoylated) in a one-step synthesis without the use of amino-protecting groups. The acylation (e.g., myristoylation) is carried out by reacting the activated fatty acid ester with the ε-amino group of the protein under basic conditions in a polar solvent. The basicity of the reaction must be sufficient to deprotonate all the free amino groups of the leptin analog. Under weakly basic conditions, all the free amino groups are not deprotonated and preferential acylation (e.g., myristoylation) of the N-terminal or α-amino groups results. After acylation (e.g., myristoylation), the product is purified by standard methods such as reverse phase hydrophobic chromatography. Thereafter, the product is recovered by standard methods such freeze drying or by crystallization.

For example, a sample of the peptide was synthesized on a Rainin Symphony synthesizer using an Fmoc/tertbutyl strategy on Rink Amide resin. The amino acids were coupled with an HCTU/DIPEA solution and the Fmoc was removed with a solution of 20% piperidine/DMF. After the automated synthesis was complete, myristic anhydride was manually added to the N-terminal of the peptide. The peptide was cleaved from the resin using a TFA cleavage cocktail. A Maldi-Tof mass spectrometry was used to check that the target mass was present. The peptide was purified using a reverse phase HPLC and a C-18 Waters Sunfire column.

The pharmacokinetics of the myristoylated peptide can be determined according to any known methods in the art. For example, the pharmacokinetics of a myristoylated leptin-related peptide can be determined by analyzing total uptake, serum half-life, and plasma clearance rate. Assays to determine total uptake, serum half-life, and plasma clearance rate are well known in the art and were used in the Examples below. The conjugation of myristic acid to [D-Leu-4]-OB3 significantly improved the pharmacokinetic profile by extending half-life from less than one hour to as long as 28 hours, depending on the route of delivery, increasing uptake, reducing the rate of plasma clearance, and enabling the minimal effective dose to be reduced 4-fold or more. The myristoylated peptides of the present invention thus provide significant advantages over un-myristoylated leptin peptides, for example, they may administered in lower dosages and with less frequency of administration. Although the present invention has been tested using SEQ ID NO: 1, the approach of the present invention may be applied to other leptin-related proteins and then tested for efficacy as described below.

Example 1

Conjugation of myristic acid to [D-Leu-4]-OB3, a biologically active leptin-related synthetic peptide amide, significantly improves its pharmacokinetic profile.

Materials and Methods

Housing of Animals

Three to four week-old male Swiss Webster mice weighing between 12 and 15 g were obtained from Charles River Laboratories (Troy, N.Y., USA). The animals were housed three per cage in polycarbonate cages fitted with stainless steel wire lids and air filters, and supported on ventilated racks (Thoren Caging Systems, Hazelton, Pa., USA) in the Albany Medical College Animal Resources Facility. The mice were maintained at a constant temperature (24° C.) with lights on from 07:00 to 19:00 h, and allowed food and water ad libitum until used for uptake studies.

Peptide Administration

MA-[D-Leu-4]OB3 was prepared commercially as a C-terminal amide by NeoBioLab (Cambridge, Mass., USA). For SC, IP and IM delivery, the peptide was dissolved in sterile phosphate buffered saline (PBS, pH 7.2) at a concentration of 0.1 mg/200 µl, a concentration 10-fold lower than that of [D-Leu-4]-OB3 previously shown to be optimum for regulating energy expenditure, glucose levels, and insulin sensitivity in two genetically obese mouse models. For oral and intranasal delivery, MA-[D-Leu-4]-OB3 was dissolved in 0.3% Intravail® (Aegis Therapeutics, San Diego, Calif., USA) reconstituted in sterile deionized water at a concentration of 0.1 mg/100 µL and 0.1 mg/10 µL, respectively. At time zero (0), a single 200 µl SC, IM, or IP injection of mouse MA-[D-Leu-4]-OB3 was given to each of three mice per time point. Intranasal delivery was achieved by lightly anesthetizing the mice with isoflurane (1-4%) and delivering 10 µl of MA-[D-Leu-4]OB3 into the nares using a Gilson® P-20 pipettor. Following peptide administration, the mice were transferred to separate cages for the designated time period.

Collection of Blood and Serum Preparation

One, two, four, six, 18, and 24 h after peptide delivery, the mice were anesthetized with isoflurane (5%) and exsanguinated by cardiac puncture. The blood was collected in sterile non-heparinized plastic centrifuge tubes and allowed to stand at room temperature for 1 h. The clotted blood was rimmed from the walls of the tubes with sterile wooden applicator sticks. Individual serum samples were prepared by centrifugation for 30 min at 2600×g in an Eppendorf 5702R, A-4-38 rotor (Eppendorf North America, Westbury, N.Y., USA), pooled by time point, and stored frozen until assayed for MA-[D-Leu-4]OB3 content. These animal procedures were approved by the Albany Medical College Animal Care and Use Committee, and were performed in accordance with relevant guidelines and regulations.

Measurement of Serum MA[D-Leu-4]-OB3

MA-[D-Leu-4]-OB3 concentrations in the pooled serum samples were measured with a competitive ELISA, developed and validated by the present inventors, with the following modification: MA-[D-Leu-4]-OB3 was used to construct the standard curve. Cross-reactivity of MA-[D-Leu-4]-OB3 with the polyclonal antibody to [D-Leu-4]-OB3 used in the ELISA was 100%. Each serum sample was assayed in duplicate. Intra- and inter-assay coefficients of variation were 0.03% and 0.2%, respectively.

Pharmacokinetic Analyses: Total Uptake (AUC)

Serum concentrations of MA-[D-Leu-4]OB3 vs. time following SC, IP, IM, oral, or intranasal delivery were plotted using the graphics program SigmaPlot 8.0 (SPSS Science, Chicago, Ill., USA). The area under each curve (AUC) was calculated with a function of this program, and expressed as ng/ml/min.

Pharmacokinetic Analyses: Serum Half-Life ($t_{1/2}$)

The period of time required for the serum concentration of MA-[D-Leu-4]OB3 to be reduced to exactly one-half of the maximum concentration achieved following IP, SC, IM, oral, and intranasal administration was calculated using the following formula:

$$t_{1/2} = 0.693/k_{elim}$$

where $k_{elim}$ represents the elimination constant, determined by plotting the natural log of each of the concentration points in the beta phase of the uptake profiles against time. Linear regression analysis of each of these plots resulted in a straight line, the slope of which represents the kelim for each delivery method.

Pharmacokinetic Analyses: Plasma Clearance (CL)

Clearance of MA-[D-Leu-4]-OB3 from the plasma following IP, SC, IM, oral, and intranasal delivery was calculated from the AUC using the following equation:

$$CL = Dose/AUC:$$

Pharmacokinetic Analyses: Apparent Volume of Distribution ($V_d$)

Because the half-life of a drug is inversely related to its clearance from the plasma and directly proportional to its volume of distribution, the apparent volume of distribution of MA-[D-Leu-4]-OB3 following ip, sc, im and intranasal delivery was calculated from its half-life and clearance using the following equation:

$$t_{1/2} = 0.693 \times V_d/CL$$

Results

The half-life of [D-Leu-4]-OB3 is normally under one hour, and the physiologically effective dose is in the milligram range. In view of the applications of [D-Leu-4]-OB3 to the treatment of human obesity and/or diabetes, it was of great importance to improve the pharmacokinetic profile of [D-Leu-4]-OB3, primarily to extend serum half-life and/or reduce the optimal effective dose. The results presented herein showed that conjugation of myristic acid to [D-Leu-4]-OB3 significantly improved its pharmacokinetic profile by (a) extending its half-life from less than one hour to as long as 28 hours, depending on the route of delivery, (b) increasing its uptake, (c) reducing the rate at which it is cleared form the plasma, and (d) enabling the minimal effective dose to be reduced 4-fold.

Uptake Profiles

Figure 2:
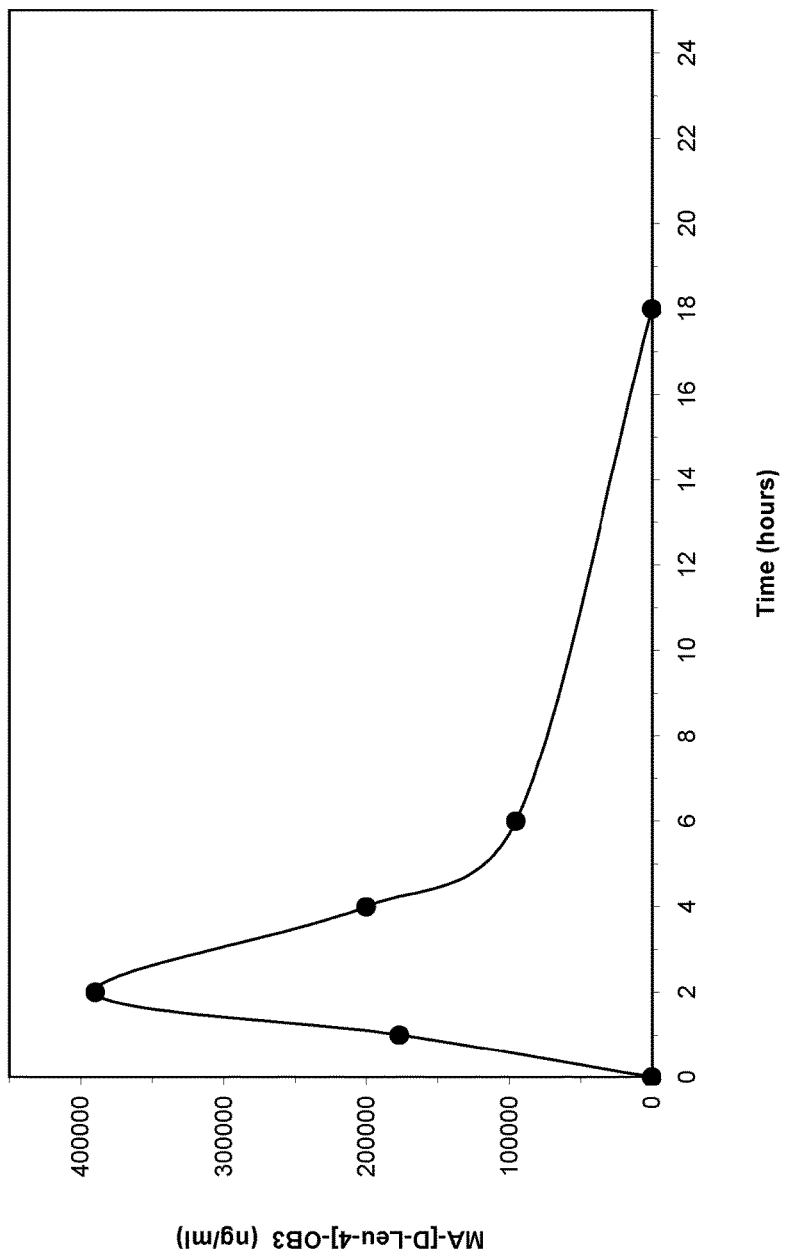
Figure 3:
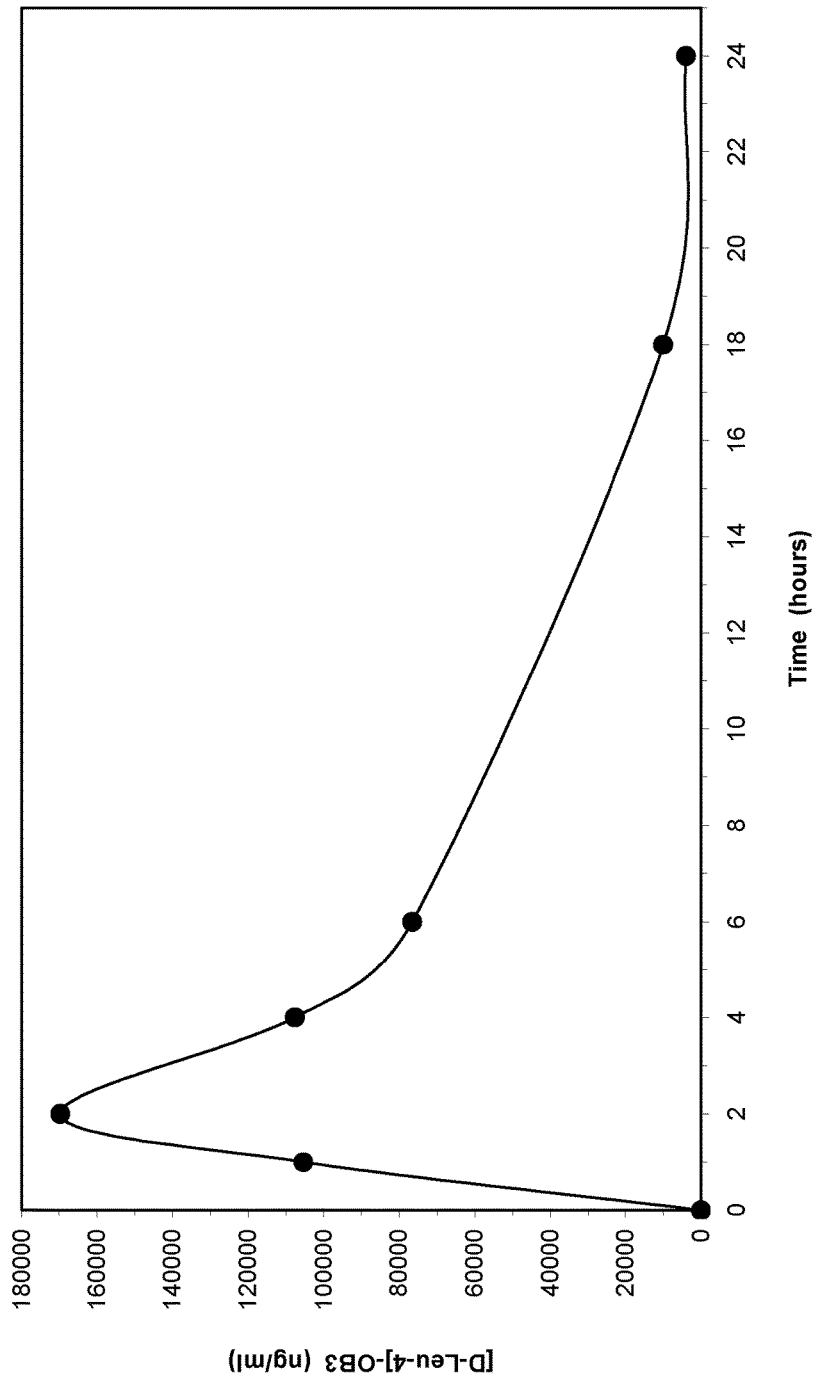
Figure 4:
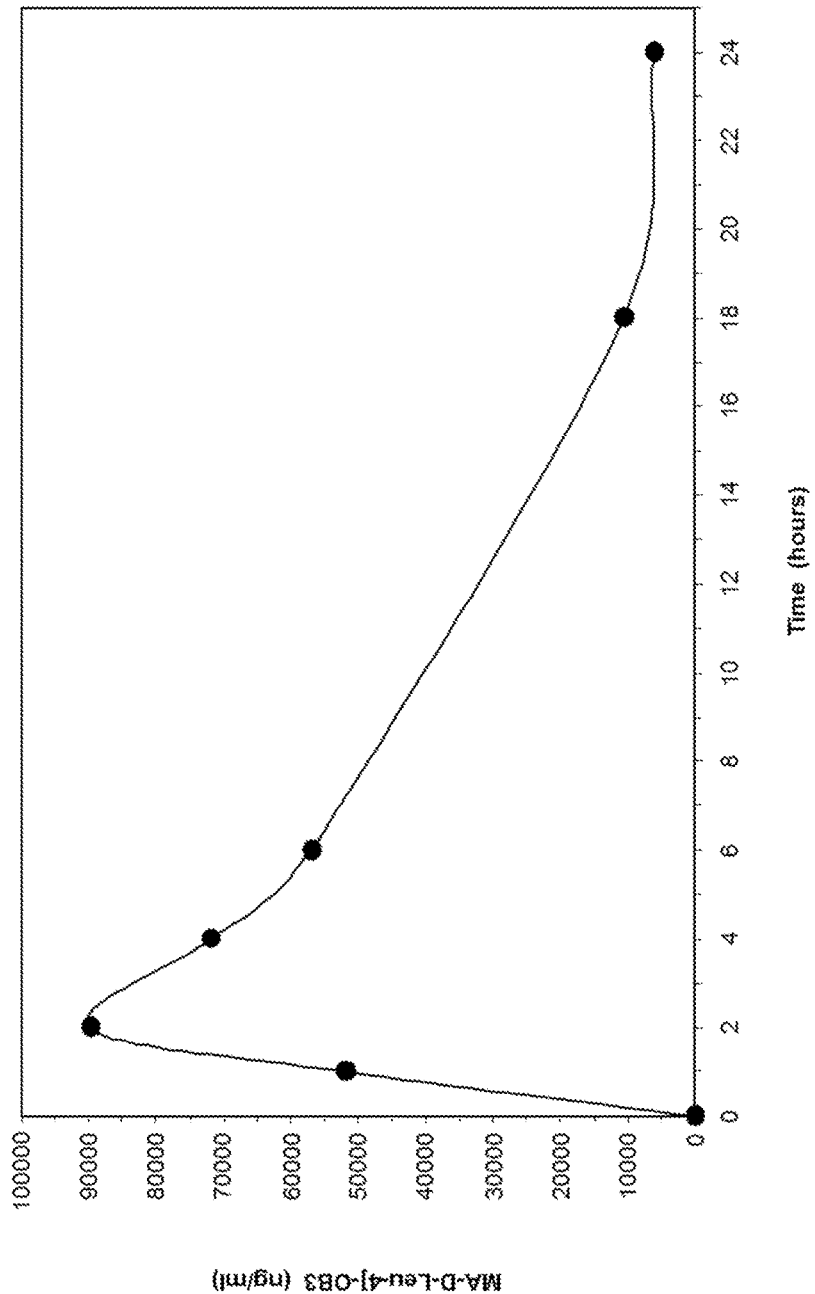
Figure 5:
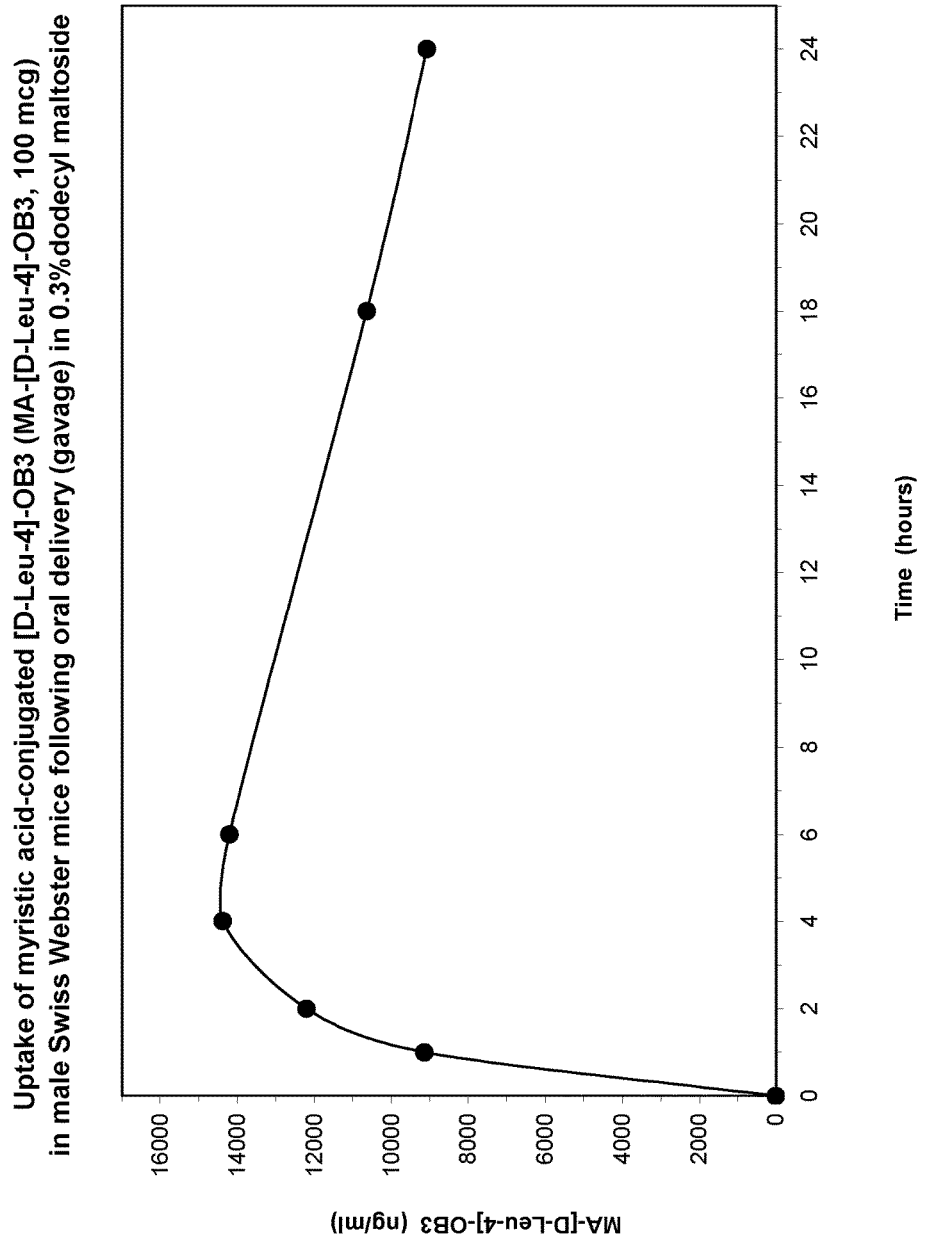
Figure 6:
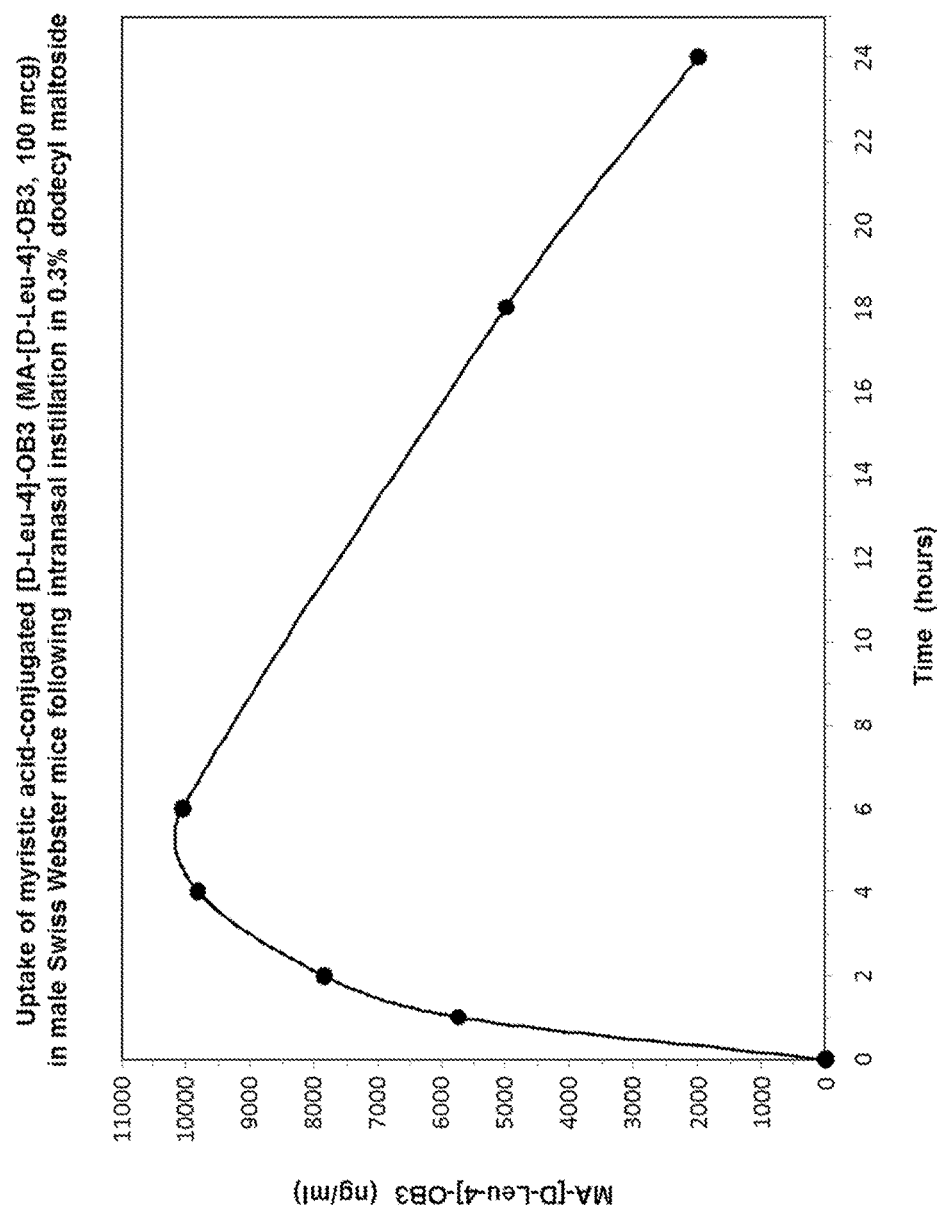
Figure 7:
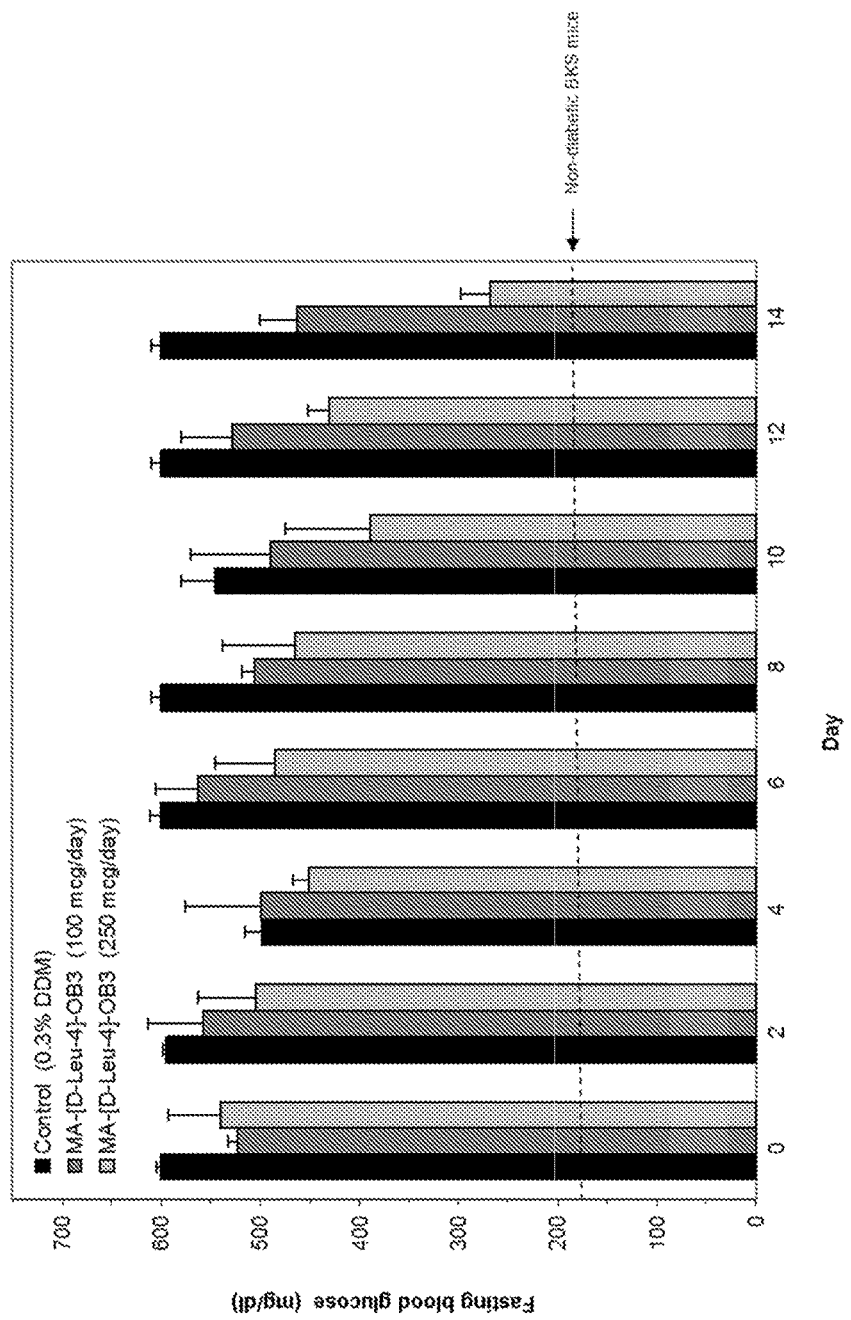
FIG. 7 is a graph showing effects of myristic acid-conjugated [D-Leu-4]-OB3 on fasting blood glucose in db/db mice following oral delivery in 0.3% dodecyl maltoside.
Figure 8:
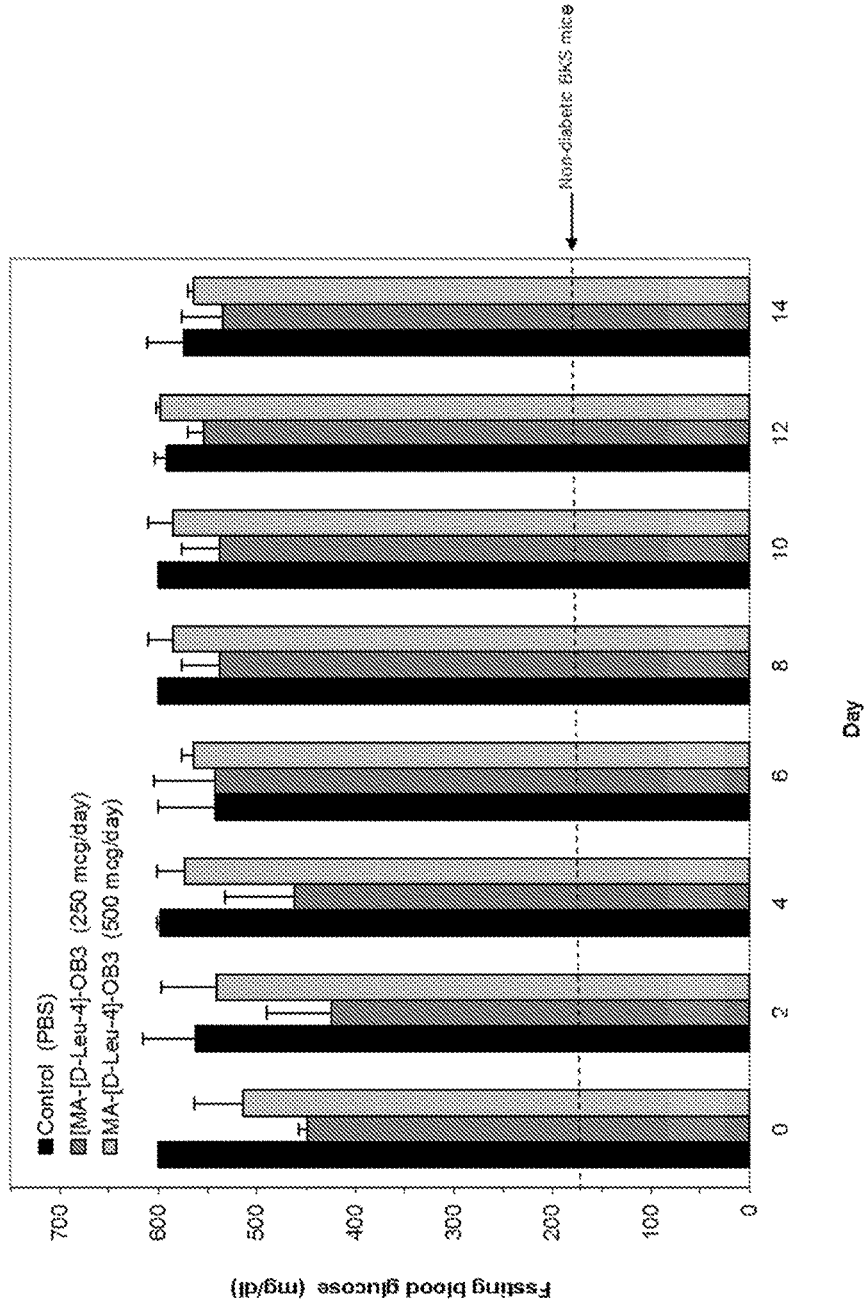
FIG. 8 is a graph showing effects of myristic acid-conjugated [D-Leu-4]-OB3 on fasting blood glucose in db/db mice following oral delivery in PBS.

The uptake profiles of MA-[D-Leu-4]OB3 following SC, IP, IM, oral, and intranasal delivery are shown in FIGS. 2-6, respectively. Maximum uptake ($C_{max}$) of MA-[D-Leu-4]-OB3 following SC, IP, and IM administration of 0.1 mg of peptide occurred at 2 hours ($t_{max}$) and rapidly decreased with time. After 18 hours, the concentration of MA-[D-Leu-4]-OB3 in the serum was reduced to near basal levels (FIGS. 2-4). The uptake profiles following oral and intranasal administration (FIGS. 5 and 6) were conspicuously different from those observed for SC, IP, or IM delivery. $C_{max}$ following oral and intranasal delivery of MA-[D-Leu-4]-OB3 was achieved at four and six hours, respectively. Twenty-four hours after oral and intranasal delivery, however, $C_{max}$ was reduced by 31% and 80%, respectively.

Total Uptake

Total uptake of MA-[D-Leu-4]-OB3 was determined by measuring the area under the uptake curve (AUC) for each delivery method. This value represents the total uptake or extent of peptide absorption into the systemic circulation, or total uptake following its administration. The AUC values following SC, IP, IM, oral, and intranasal delivery were 1,829,225 ng/ml/min, 1,212,330 ng/ml/min, 842,374 ng/ml/min, 278,460 ng/ml, and 158,426 ng/ml. respectively. From these values, the relative bioavailabilities following intranasal, oral, IM, IP and SC delivery were calculated to be 1.0, 1.8, 5.3, 7.7 and 11.7, respectively.

Elimination Constants ($k_{elim}$) and Serum Half-Life ($t_{1/2}$)

Elimination constants for MA-[D-Leu-4]-OB3 following SC, IP, IM, oral, and intranasal delivery were calculated as described in Materials and Methods, and were determined to be −0.350, −0.155, −0.117, −0.024, and −0.085, respectively. The serum half-life of MA-[D-Leu-4]-OB3 following SC, IP, IM, oral, and intranasal administration was 2.0, 4.1, 5.5, 28.9, and 8.2 hours, respectively.

Plasma Clearance (CL) and Apparent Volume of Distribution ($V_d$)

Clearance of MA-[D-Leu-4]-OB3 from the plasma following SC, IP, IM, oral, and intranasal administration was 0.05, 0.08, 0.12, 0.36, and 0.63 ml/min, respectively. The apparent volume of distribution of MA-[D-Leu-4]-OB3 following SC, IP, IM, oral, and intranasal delivery 8.6, 30.9, 61.3, 900.8, and 447.0 ml, respectively. These pharmacokinetic parameters, and those previously described for [D-Leu-4]-OB3 are summarized in Table 1 below.

TABLE 1

Pharmacokinetic profiles of [D-Leu-4]-OB3 (1 mg)[1] and MA-[D-Leu-4]-OB3 (0.1 mg) following SC, IP, IM, oral, and intranasal delivery

| Delivery | Parameter | [D-Leu-4]-OB3 | MA-[D-Leu-4]-OB3 |
|---|---|---|---|
| [2]SC | $C_{max}$ (ng/ml) | 35,063 | 389,490 |
| | $T_{max}$ | 5 min | 2 h |
| | AUC (ng/ml/min) | 1,182,498 | 1,829,225 |
| | $k_{elim}$ | −0.020 | −0.350 |
| | $t_{1/2}$ | 34 min | 2.0 h |
| | Plasma CL (ml/min) | 0.85 | 0.05 |
| | $V_d$ (ml) | 42.9 | 8.6 |
| [2]IP | $C_{max}$ (ng/ml) | 22,519 | 169,620 |
| | $T_{max}$ | 5 min | 2 h |
| | AUC (ng/ml/min) | 1,072,270 | 1,212,330 |
| | $k_{elim}$ | −0.014 | −0.155 |
| | $t_{1/2}$ | 49 min | 4.5 h |
| | Plasma CL (ml/mm) | 0.93 | 0.08 |
| | $V_d$ (ml) | 65.5 | 30.9 |
| [2]IM | $C_{max}$ (ng/ml) | 46,566 | 89,750 |
| | $T_{max}$ | 5 min | 2 h |
| | AUC (ng/ml/min) | 1,481,060 | 842.374 |
| | $k_{elim}$ | −0.023 | −0.117 |
| | $t_{1/2}$ | 36 min | 5.9 h |
| | Plasma CL (ml/min) | 0.68 | 0.12 |
| | $V_d$ (ml) | 29.4 | 60.3 |
| [3]Oral | $C_{max}$ (ng/ml) | 8,574 | 14,373 |
| | $T_{max}$ | 50 min | 4 h |
| | AUC (ng/ml/min) | 552,710 | 278,460 |
| | $k_{elim}$ | −0.034 | −0.024 |
| | $t_{1/2}$ | 20 min | 28.9 h |
| | Plasma CL (ml/min) | 1.81 | 0.36 |
| | $V_d$ (ml) | 47.9 | 900.8 |
| [3]Intranasal | $C_{max}$ (ng/ml) | 91,732, 36,069 | 10,047 |
| | $T_{max}$ | 10 min, 60 min | 6 h |
| | AUC (ng/ml/min) | 4,336,963 | 158,426 |
| | $k_{elim}$ | −0.090, −0.020 | −0.85 |
| | $t_{1/2}$ | 41 min | 8.2 h |
| | Plasma CL (ml/min) | 1.37 | 0.63 |
| | $V_d$ (ml) | 15.4 | 447.0 |

[1]Data taken from prior research
[2]Delivered in PBS
[3]Delivered in 0.3% DDM

In previous studies with [D-Leu-4]-OB3, although repeatedly demonstrating its leptin-like effects on energy balance and glucose homeostasis, high concentrations (millimolar range) and multiple daily doses were required for a sustained response, regardless of the route of delivery. It was essential, therefore, for the present invention improve the pharmacokinetics of [D-Leu-4]-OB3 for its human application. Specifically, increasing the bioavailability of [D-Leu-4]-OB3, extending its half-life, and reducing the rate at which it is cleared from the systemic circulation were sought. Such improvements make it possible to reduce the size and frequency of the dose of [D-Leu-4]-OB3 delivered, while sustaining or improving its efficacy.

The conjugation of myristic acid to [D-Leu-4]-OB3 according to the present invention prevents a valid approach for improving the pharmacokinetic profile of [D-Leu-4]-OB3. When delivered by IP, SC, or IM injection, or orally by gavage, the maximum uptake ($C_{max}$) of MA-[D-Leu-4]-OB3 was dramatically higher than that of [D-Leu-4]-OB3, even at a dose that was 10-fold lower. The biphasic uptake of [D-Leu-4]-OB3, which was observed following intranasal instillation, however, was not observed following intranasal delivery of MA-[D-Leu-4]-OB3, a phenomenon which may be related to the lower dose administered. This change in the uptake profile of MA-[D-Leu-4]-OB3 following intranasal instillation suggests a single site of absorption at which the maximal concentration of peptide is achieved much later when compared to the two peaks observed in the uptake profile of [D-Leu-4]-OB3, $T_{max}$ at 6 h vs. 10 and 60 min, respectively.

As indicated by the data, absorption of MA-[D-Leu-4]-OB3 occurs slowly over a period of 2 to 6 hours depending on the route of administration, compared to 5 to 60 minutes for [D-Leu-4]-OB3. These findings indicate that myristic acid conjugation facilitates the uptake of higher concentrations of MA-[D-Leu-4]-OB3 compared to [D-Leu-4]-OB3, but at a slower rate. Although this pattern of absorption did not appear to elevate total uptake (AUC) of MA[D-Leu-4]-OB3 in all delivery methods used, it did prolong the time during which elevated levels of the peptide were present in the systemic circulation.

Worthy of special note, and directly related to prolonging the biological activity of MA-[D-Leu-4]-OB3, is its longer half-life and slower clearance from the plasma compared to [D-Leu-4]-OB3 was observed following each delivery method utilized in this study. This pattern can sustain the biological activity of MA-[D-Leu-4]-OB3 over a longer period of time when compared to [D-Leu-4]-OB3, which is rapidly elevated in the serum and rapidly cleared. Results from the oral efficacy studies in db/db mice, in which lower doses of MA-[D-Leu-4]-OB3 than previously used with [D-Leu-4]-OB3 were delivered, indicated that this is the case.

The myristic acid conjugation of [D-Leu-4]-OB3 according to the present invention thus significantly improves its pharmacokinetic profile. The data also indicate that MA-[D-Leu-4]-OB3 can be used as an oral, noninvasive, and safe therapeutic approach for the management of obesity and/or diabetes in humans.

Example 2

Studies comparing the effects of oral delivery of myristic acid-conjugated [D-Leu-4]-OB3 in PBS or 0.3% dodecyl maltoside (DDM, Intravail®) on fasting blood glucose in six to seven week-old male BKS.Cg-Dock7$^m$+/+Lepr$^{db}$/J diabetic db/db mice.

Male db/db mice were given increasing concentrations of MA-[D-Leu-4]-OB3 in either PBS or DDM orally by gavage once daily in the evening for 14 consecutive days. Fasting (8 hours) blood glucose levels were measured every other day using an Accu-Chek Nano glucose meter (Roche, Indianapolis, Ind.). After 14 days of treatment, blood glucose levels in mice receiving MA-[D-Leu-4]-OB3 (250 or 500 mcg/day) in PBS were unchanged from those in control mice receiving PBS alone. Blood glucose levels in db/db mice receiving either 100 or 250 mcg/day in 0.3% DDM, however, were significantly reduced to levels seen in non-diabetic BKS mice by the end of the 14-day treatment period in mice treated with 250 mcg/day.

These results indicate that MA-[D-Leu-4]-OB3, at a concentration four-fold lower than that used in our previous studies with [D-Leu-4]-OB3, is effective in reducing blood glucose levels when delivered orally in DDM. These results were consistent with the pharmacokinetic data, which indicated enhanced uptake, slower clearance, and longer half-life of MA-[D-Leu-4]-OB3 in DDM compared to that of [D-Leu-4]-OB3 in DDM.

Example 3

A study demonstrating the efficacy of myristic acid-conjugated [D-Leu-4]-OB3 (MA-[D-Leu-4]-OB3) on body weight gain and glycemic control in a mouse model of insulin-deficient diabetes.

Objective

Streptozotocin (STZ)-induced male Swiss Webster mice were used in these studies to examine the effects of MA-[D-Leu-4]-OB3 on body weight gain and insulin sensitivity in an insulin-deficient mouse model of diabetes. Using this model, the insulin sensitizing effects of MA-[D-Leu-4]-OB3 was compared with those of another well-characterized insulin-sensitizing drug, metformin.

Materials and Methods

Seven-week old male Swiss Webster mice were rendered hyperglycemic with a single intraperitoneal (ip) dose of 150 mg/kg STZ. Fasting blood glucose levels were measured prior to STZ treatment to establish normal (non-diabetic) glucose levels, and every day thereafter to assess hyperglycemia. Fasting blood glucose levels were routinely 3- to 4-fold higher than normal 4-5 days after STZ treatment.

Detemir insulin (Levemir®, Novo Nordisk, Malov, Denmark) delivery pens were used to dispense 0.025 U/100 µL phosphate buffered saline (PBS), and delivered by subcutaneous (sc) injection twice daily between 8:00 and 9:00 a.m. and 4:00 and 5:00 p.m. for 14 days. MA-[D-Leu-4]-OB3 (NeoBiolab, Cambridge, Mass.) and metformin (Sigma Aldrich, St. Louis, Mo.) were dissolved in 0.3% dodecyl maltoside (DDM, Intravail®, Aegis Therapeutics, San Diego, Calif.) reconstituted in sterile deionized water, and delivered twice daily by oral gavage between 8:00 h and 9:00 h and 16:00 h and 17:00 h at a concentration of 5 mg/kg/100 µL or 100 mg/kg/100 uL, respectively, for 14 days.

On day zero and each day thereafter, food and water intake were measured, and the mice were weighed in the morning between 8:00 h and 9:00 h. To assure fasting (8 hour) glucose levels on the days blood glucose was measured, food was removed from the cages between 8:00 h and 9:00 h and replaced immediately after measurement.

Results

The effects of insulin alone, or in combination with MA-[D-Leu-4]-OB3 or metformin, on body weight gain in STZ-induced hyperglycemic male SW mice are shown in FIG. 9 and Table 2 below:

TABLE 2

Effects of detemir insulin alone, or in combination with MA-[D-Leu-4]-OB3 or metformin, on body weight gain, food and water intake, and blood glucose levels in STZ-induced hyperglycemic male Swiss Webster mice

|  | DDM | MA-[D-Leu-4]-OB3 | Detemir insulin | Detemir insulin + MA-[D-Leu-4]-OB3 | Detemir insulin + Metformin |
|---|---|---|---|---|---|
| Initial body weight (gm) | 27.7 ± 4.1 | 24.8 ± 1.4 | 24.8 ± 2.2 | 26.8 ± 2.3 | 24.0 ± 1.3 |
| Final body weight (gm) | 31.0 ± 4.0 | 26.8 ± 1.6 | 28.8 ± 3.0 | 30.0 ± 1.3 | 26.4 ± 2.0 |
| % of initial | 111.9 | 108.1 | 116.1 | 111.9 | 110 |
| Change (gm) | +3.3 | +2.0 | +4.0 | +3.2 | +2.4 |
| Cumulative food intake (gm/mouse) | 121.7 ± 1.2 | 103.3 ± 2.3 | 106.4 ± 2.0 | 105.2 ± 3.1 | 109.5 ± 2.1 |
| Cumulative water intake (mL/mouse) | 540.8 ± 5.8 | 452.5 ± 6.4 | 542.8 ± 11.2 | 472.6 ± 8.3 | 403.2 ± 12.1 |
| Initial blood glucose (mg/dL) | 522.3 ± 5.0 | 507.0 ± 6.0 | 551.0 ± 5.0 | 568.7 ± 7.0 | 506.5 ± 13.0 |
| Final blood glucose (mg/dL) | 568.3 ± 4.1 | 501.0 ± 12.3 | 351.0 ± 11.3 | 232.8 ± 7.0 | 124.6 ± 15.0 |
| % of initial | 108.8 | 98.8 | 63.7 | 40.9 | 24.6 |
| Change (mg/dL) | 46 | −6 | −200 | −335.9 | −381.9 |

Mice given DDM alone were 11.9% heavier at the end of the 14-day test period, while mice receiving 0.05 U insulin daily were 16.1% heavier. Mice receiving MA-[D-Leu-4]-OB3 alone were only 8.1% heavier. When MA-[D-Leu-4]-OB3 was given in combination with insulin, the body weight gain induced by insulin was reduced to that observed in untreated mice (11.9%). When metformin was given in combination with insulin, body weight gain increased by only 10.0%.

The effects of insulin, in the absence or presence of MA-[D-Leu-4]-OB3 or metformin, on fasting blood glucose in STZ-induced hyperglycemic mice are shown in FIG. 10 and Table 2. Fasting blood glucose levels in normal SW mice remained stable (150-170 mg/dl) during the 14 day study, while fasting blood glucose levels in STZ-treated mice receiving DDM alone ranged between 500 and 600 mg/dL. 0.05 U detemir insulin reduced blood glucose levels by 64.0%, but not to a normal range. MA-[D-Leu-4]-OB3 alone had very little effect on fasting blood glucose levels. When given in combination with MA-[D-Leu-4]-OB3 or metformin, the anti-hyperglycemic effect of 0.05 U detemir insulin was amplified. Within two days, fasting blood glucose levels in mice given MA-[D-Leu-4]-OB3 in combination with insulin were nearly normalized, and remained so throughout the study. No hypoglycemic events were noted. Similar results were observed when metformin was given in combination with insulin. After 6 days or treatment, however, the mice receiving metformin became increasingly hypoglycemic.

Conclusions

The results of this study indicate that MA-[D-Leu-4]-OB3, when given orally in combination with subcutaneously administered insulin, prevents the body weight gain associated with insulin pharmacotherapy. The results further suggest that MA-[D-Leu-4]-OB3, in this insulin-deficient mouse model of diabetes, is as good as or surpasses metformin in preventing the body weight gain induced by exogenous insulin, and in enhancing tissue sensitivity to insulin.

The insulin sensitizing effect of MA-[D-Leu-4]-OB3 is further supported by the observation that in this mouse model of insulin deficiency, contrary to what has been seen previously with [D-Leu-4]-OB3 in hyper-insulinemic ob/ob and db/db mice, and with MA-[D-Leu-4]-OB3 in db/db mice, MA-[D-Leu-4]-OB3 alone was unable to significantly reduce fasting blood glucose levels. These levels, only 1.2% lower at the end of the 14-day test period than they were at the beginning of the study, confirm that endogenous insulin production was severely impaired by STZ treatment.

This data reflects an absolute dependence on the presence of insulin in order for MA-[D-Leu-4]-OB3 to exert its influence on blood glucose levels. This conclusion is further supported by the observation that MA-[D-Leu-4]-OB3 (at 0.25 mg/kg/day) when given in combination with exogenous insulin, was able to normalize blood glucose levels within the first two days of the study.

Regarding the efficacy of MA-[D-Leu-4]-OB3 on glucose homeostasis in this mouse model, worthy of special note is the fact that although MA-[D-Leu-4]-OB3 and metformin were both able to reduce blood glucose to within normal levels when given in combination with exogenous insulin, the dose of MA-[D-Leu-4]-OB3 was 20-fold lower than that of metformin (10 mg/kg/day vs. 200 mg/kg/day, respectively). The data indicates that MA-[D-Leu-4]-OB3 may be 20 times more effective than metformin on a mass basis in improving insulin sensitivity in this mouse model of insulin-deficiency, and 6.1 times more effective on a molar basis.

In other embodiments, the invention can be a pharmaceutical compound comprising any one of cyclohexylvaleroyl, acyl-glutamyl, lauroyl, 2-succinylamido myristic acid, 2-succinylamidoethyloxy palmitic acid, myristoyl-α-glutamyl, myristoyl-α-glutamyl-glycyl, choloyl, 7-deoxycholoyl, lithocholoyl, lithocholoyl-glutamyl, 4-benzoyl-phenylalanine, L-thyroxyl, suberoyl-D-thyroxine, 3,3',5,5'-tetraiodothyroacetyl, cyclohexylvaleroyl conjugated to a leptin-related peptide. The leptin related peptide can be one of AVPIQKVQDDTKTLI (SEQ ID NO: 2); TKTLIKTIVTRINDI (SEQ ID NO: 3); RINDISHTQSVSAKQ (SEQ ID NO: 4); VSAKQRVTGLDFIPG (SEQ ID NO: 5); DFIPGLHPILSLSKM (SEQ ID NO: 6); SLSKMDQTLAVYQQV (SEQ ID NO: 7); VYQQVLTSLPSQNVL (SEQ ID NO: 8); SQNVLQIANDLENLR (SEQ ID NO: 9); DLLHLLAFSKSCSLP (SEQ ID NO: 10); SCSLPQTSGLQKPES (SEQ ID NO: 11); QKPESLDGVLEASLY (SEQ ID NO: 12); EASLYSTEVVALSRL (SEQ ID NO: 13); ALSRLQGSLQDILQQ (SEQ ID NO: 14); or DILQQLDVSPEC (SEQ ID NO: 15).

What is claimed is:

1. A pharmaceutical compound, comprising myristic acid conjugated to an N-terminal serine residue of a leptin-related peptide having a sequence selected from the group consisting of SEQ. ID NO: 1 and SEQ. ID NO: 16.

2. The pharmaceutical compound of claim 1, wherein the leptin-related peptide contains at least one D-isoform amino acid.

3. The pharmaceutical compound of claim 2, wherein the leptin-related peptide is D-substituted at Leu-4.

4. A method of treating a subject for a condition associated with the dysregulation of homeostasis of body mass, comprising the step of administering a pharmaceutically effective amount of a molecule of myristic acid conjugated to an N-terminal serine residue of a leptin-related peptide having a sequence selected from the group consisting of SEQ. ID NO: 1 and SEQ. ID NO: 16.

5. The method of claim 4, wherein the leptin-related peptide contains at least one D-isoform amino acid.

6. The method of claim 5, wherein the leptin-related peptide is D-substituted at Leu-4.

7. The method of claim 4, wherein the condition is obesity, hyperglycemia, hyperinsulinemia, hyperphagia, thyroid dysfunction, infertility, osteoporosis, cancer or diabetes.

* * * * *